(12) United States Patent  (10) Patent No.: US 8,133,212 B2
Takada et al.  (45) Date of Patent: Mar. 13, 2012

(54) DISPOSABLE DIAPER

(75) Inventors: Naoko Takada, Kagawa-ken (JP);
Hironao Minato, Kagawa-ken (JP);
Yuko Matsuda, Kagawa-ken (JP);
Yoshitaka Mishima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 1002 days.

(21) Appl. No.: 11/690,233

(22) Filed: Mar. 23, 2007

(65) Prior Publication Data
US 2007/0239128 A1   Oct. 11, 2007

(30) Foreign Application Priority Data
Apr. 6, 2006  (JP) ................. 2006-105511

(51) Int. Cl.
*A61F 13/15* (2006.01)
*A61F 13/20* (2006.01)
(52) U.S. Cl. ........ 604/385.19; 604/385.201; 604/385.27
(58) Field of Classification Search ............. 604/385.19, 604/385.201, 385.22, 385.24–385.27
See application file for complete search history.

(56) References Cited

U.S. PATENT DOCUMENTS

| | | | | |
|---|---|---|---|---|
| 5,342,858 A * | 8/1994 | Litchholt et al. | ......... | 521/98 |
| 2001/0016719 A1 | 8/2001 | Mishima | | |
| 2005/0107761 A1 | 5/2005 | Mishima et al. | | |
| 2005/0228358 A1 | 10/2005 | Mishima et al. | | |
| 2005/0234421 A1 | 10/2005 | Mishima et al. | | |
| 2006/0184151 A1 | 8/2006 | Onishi et al. | | |

FOREIGN PATENT DOCUMENTS

| | | |
|---|---|---|
| EP | 1084688 | 3/2001 |
| JP | 8196565 | 8/1996 |
| JP | 08-322878 | 12/1996 |
| JP | 2001-224628 | 8/2001 |
| WO | 02067833 | 9/2002 |

OTHER PUBLICATIONS

JP 2004-321460 A to Onishi et al, English translation.*
Supplementary European Search Report for European Application No. 07738729.8 mailed Aug. 30, 2010.

* cited by examiner

*Primary Examiner* — Melanie Hand
(74) *Attorney, Agent, or Firm* — Lowe, Hauptman, Ham & Berner, LLP

(57) ABSTRACT

In a disposable diaper, the crotch region is divided by a front folding guide and a rear folding guide into a front section, a rear section and an intermediate section. The crotch region is provided on the side of its inner surface with a pair of contracting members extending in a longitudinal direction and spaced from each other. Front portions of the respective contracting members are fixed to the inner surface of the diaper in positions anterior to a line bisecting a longitudinal dimension of the intermediate section, while rear portions of the respective contracting members are fixed to the inner surface of the diaper in positions posterior to the intermediate section, so that intermediate portions of the respective contracting members may be spaced from the inner surface of the diaper and elastically contractible in the longitudinal direction.

15 Claims, 10 Drawing Sheets

DISPOSABLE DIAPER

BACKGROUND OF THE INVENTION

The present invention relates generally to a disposable diaper and more particularly to a disposable diaper provided with a feces receiving space.

Disposable diapers provided with a feces receiving space is well known. For example, a disposable diaper disclosed in Japanese Unexamined Patent Application Publication No. 2001-224628 (hereinafter referred to as "REFERENCE") is provided on the inner surface thereof with a pair of cushioning pad members spaced from each other in a longitudinal direction of the diaper and a pair of side sheets attached to these paired pad members along opposite sides thereof so as to extend in parallel to each other in the longitudinal direction and to be spaced from each other in the transverse direction. The pad members define protuberances on the inner surface of the diaper and, on the inner surface of the diaper, the paired pad members cooperate with the paired side sheets to form a feces receiving space opened toward the diaper wearer's anus.

In the case of the diaper disclosed by REFERENCE, a depth of the feces receiving space depends on a thickness (i.e., height) of the pad members. Therefore, the pad members of increased thickness may be used to increase the depth of the feces receiving space. However, this known diaper is adapted to be used with these pad members forming the protuberances on the inner surface of the diaper. Specifically, the thicker the pad members are, the more significant the irregularity on the inner surface of the diaper becomes, making it difficult for the diaper to come in smooth contact with the wearer's skin. Such diaper may locally press the wearer's skin to the degree at which the wearer may experience a discomfortable feeling to wear the diaper.

SUMMARY OF THE INVENTION

In view of the problem as has been described above, it is an object of the present invention to provide a disposable diaper free from a likelihood that the wearer might experience a discomfortable feeling to wear the diaper even if the depth of the feces receiving space is increased.

According to the present invention, there is provided a disposable diaper having a front waist region, a rear waist region and a crotch region therebetween, these respective regions having an inner surface facing a wearer's skin and outer surface facing the wearer's garment, the crotch region being provided along lateral edges thereof with leg-encircling elastic members attached thereto, respectively, and the crotch region being formed on the inner surface with a feces receiving space defined between the leg-encircling elastic members extending along the lateral edges, and an opening of the feces receiving space.

The present invention comprises the crotch region being divided by a front folding guide and a rear holding guide extending in parallel to each other in a transverse direction orthogonal to a longitudinal direction thereof into a front portion, a rear portion and an intermediate portion so that the front portion and the intermediate portion are foldable along the front folding guide while the intermediate portion and the rear portion are foldable along the rear folding guide.

The inner surface of the crotch region is provided between the leg-encircling elastic members extending along the lateral edges with a pair of contracting means spaced from each other in the transverse direction and extending across said intermediate portion in parallel to each other in the longitudinal direction so as to be elastically contractile.

The contracting means respectively comprise front and rear sections with respect to the longitudinal direction and intermediate sections extending between the front and rear sections wherein the front sections are fixed to the inner surface at positions anterior to a line bisecting the intermediate region in the longitudinal direction, the rear sections are fixed to the inner surface at positions posterior to the intermediate section and the intermediate sections are left free from the inner surface so as to be elastically contractile in the longitudinal direction.

Upon contraction of the contracting means, the crotch region is locally folded downward in the longitudinal direction along the front folding guide and the rear folding guide to form, between a pair of the contracting means in a vicinity of the intermediate section, the feces receiving space having its inner wall defined by the inner surface.

According to one preferred embodiment of the invention, the intermediate section includes a block-shaped elastic member allowing the intermediate section to be elastically deformed.

According to another preferred embodiment of the invention, the block-shaped elastic member is formed by any one of selected from a group of a sheet made of material such as foamed polyurethane, foamed polyethylene, foamed polystyrene, natural rubber and synthetic rubber, an assembly of crimped synthetic fiber and an assembly of plural synthetic fibers straightened in parallel one to another.

According to still another preferred embodiment of the invention, the contracting means comprise a pair of strip-shaped sheets adapted to be elastically stretchable, these paired strip-shaped sheets being provided to extend in the longitudinal direction in parallel to each other and in elastically stretchable condition, each of the strip-shaped sheets having, in addition to the front section, the rear section and the intermediate section, an inner side edge and an outer side edge lying nearer to an associated outer side edge and to a central line of the crotch region, respectively, and the front section and the rear section are fixed to the inner surface so as to form the opening between the inner side edges of respective the strip-shaped sheets.

According to yet another preferred embodiment of the invention, the contracting means are formed by the strip-shaped sheets each being non-stretchable or inelastically stretchable and thread-like elastic members attached in a stretched state to the strip-shaped sheets, these paired strip-shaped sheets being provided to extend in the longitudinal direction in parallel to each other and in elastically stretchable condition, each of the strip-shaped sheets having, in addition to the front section, the rear section and the intermediate section, an inner side edge and an outer side edge lying nearer to the associated outer side edge and to the central line of the crotch region, respectively, the elastic members being attached to the inner side edges, and the front section and the rear section are fixed to the inner surface so as to form the opening between the inner side edges of respective the strip-shaped sheets.

According to further another preferred embodiment of the invention, the strip-shaped sheets are fixed to the inner surface along the outer side edges, respectively.

According to an alternatively preferred embodiment of the invention, the contracting means comprises an elastically stretchable single sheet having the front section, the rear section, the intermediate section and a through-hole provided in the middle in the transverse direction so as to define the opening, the sheet being stretched in the longitudinal direction and fixed, in such stretched state, to the inner surface at the front section and the rear section while the intermediate section is left free from the inner surface along a peripheral edge of the through-hole.

According to another alternatively preferred embodiment of the invention, the contracting means comprises an elastically stretchable single sheet having the front section, the rear section, the intermediate section and a through-hole provided in a middle in the transverse direction so as to define the opening, the sheet being fixed to the inner surface at the front section and the rear section and, in a vicinity of lateral edges of the through-hole extending in the longitudinal direction, elastic members being attached in a stretched state to the single sheet so as to leave the intermediate section free from the inner surface along the peripheral edge of the through-hole.

In the case of the disposable diaper according to the present invention, the crotch region is locally folded along the front folding guide and the rear folding guide and the feces receiving space is formed by a part of the crotch region as the contracting means contract in the longitudinal direction. The paired parallel contracting means spaced from each other in the transverse direction of the crotch region can define the opening for the feces receiving space.

In the case of the disposable diaper according to the embodiment wherein the intermediate portion of the crotch region includes the block-shaped elastic member, even if the feces receiving space is deformed as the wearer's body weight bears downward on the crotch region, the feces receiving space is able to restore its initial shape immediately after the crotch region has been released from the wearer's body weight. While the block-shaped elastic member may be selectively formed using any one of a sheet material such as foamed polyurethane, foamed polyethylene, foamed polystyrene, natural rubber or synthetic rubber and an assembly of crimped synthetic fiber, the sheet made of foamed plastic such as foamed polyurethane, foamed polyethylene or foamed polystyrene may be used to trim a weight of the diaper.

In the case of the disposable diaper according to the embodiment wherein the elastically stretchable strip-shaped sheet is used as the contracting means, such strip-shaped partially covers the feces receiving space so as to protect the wearer's skin from being contaminated with feces already received within the feces receiving space.

In the case of the disposable diaper according to the embodiment wherein the elastically stretchable strip-shaped sheets provided with the thread-like elastic members bonded in stretched state thereto are used as the contracting means, it is possible to reduce the material cost for the contracting means.

In the case of the disposable diaper according to the embodiment wherein the outer side edges of the respective strip-shaped sheets serving as the contracting means are fixed to the inner surface of the diaper, body fluids tending to flow on the inner surface of the diaper can be held back to improve a desired leak-proof effect.

In the case of the disposable diaper according to the embodiment wherein the paired strip-shaped sheets as the contracting means are replaced by the single sheet formed in its middle in the transverse direction with the through-hole, it is possible to protect the wearer's skin in a wide range from being contaminated with feces. This strip-shaped single sheet may be elastically stretchable or non-stretchable or inelastically stretchable.

DETAILED DESCRIPTION OF THE PREFERRED EMBODIMENTS

Details of a disposable diaper according to the present invention will be more fully understood from the description of several embodiments given hereunder with reference to the accompanying drawings.

Figure 1:
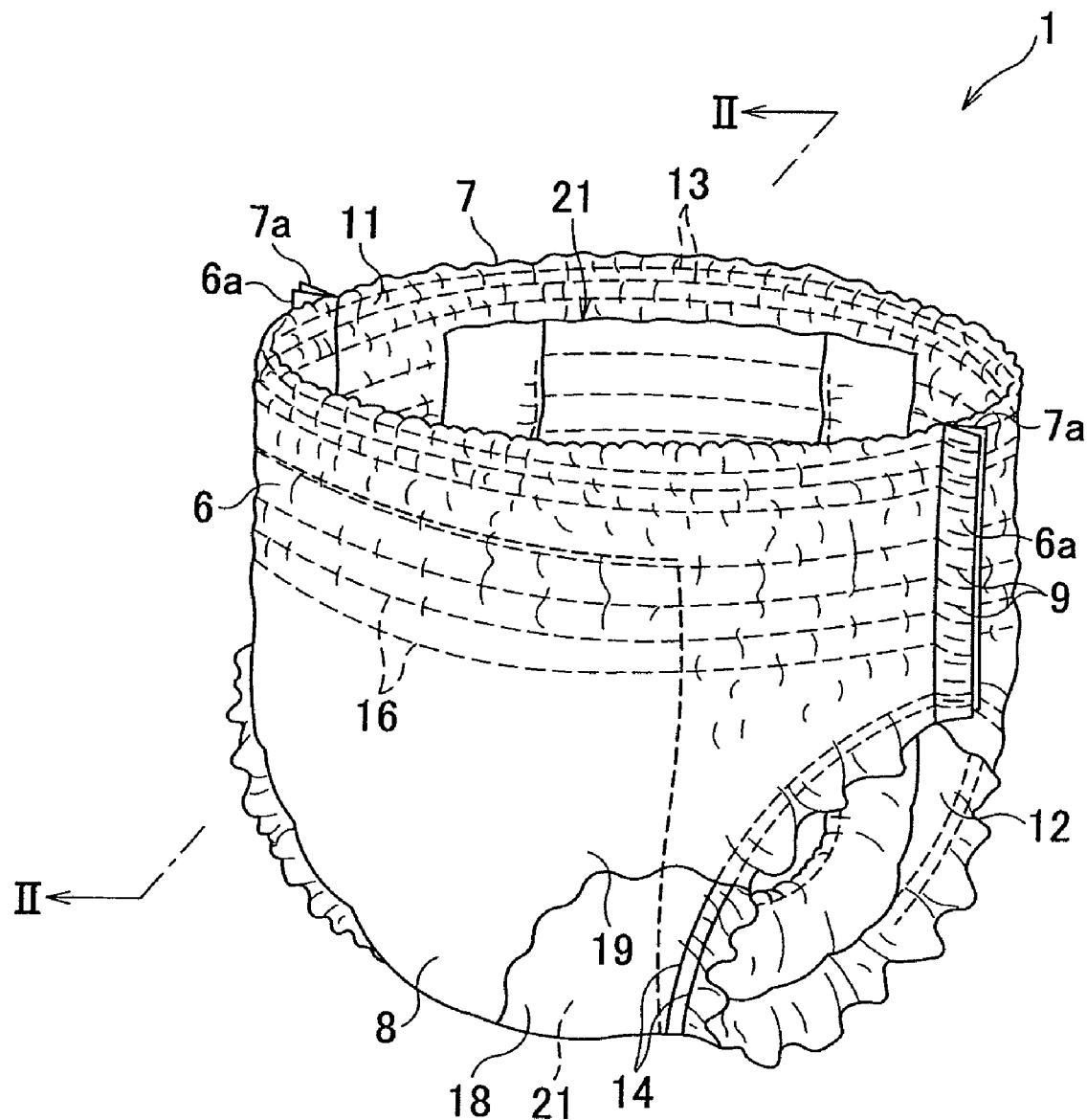
FIG. 1 is a perspective view, partially broken away, showing a disposable diaper.

FIG. 1 is a perspective view, partially broken away, showing a disposable diaper 1. The diaper 1 is of pull-on type and composed of a crotch region 8, a front waist region 6 extending forward from the crotch region 8 and a rear waist region 7 extending rearward from the crotch region 8. The front and rear waist regions 6, 7 are put flat together along lateral edges 6a, 7a thereof and sealed together at sealing spots 9 arranged intermittently in a vertical direction as viewed in FIG. 1 along these opposite edges 6a, 7a. These front and rear waist regions 6, 7 cooperate with each other to form a waist-hole 11 while these front and rear waist regions 6, 7 cooperate with the crotch region 8 to form a pair of leg-holes 12. A waist-encircling elastic member 13 consisting of three rubber threads is attached in a stretched state to a peripheral edge of the waist-hole 11 while leg-encircling elastic members 14 each consisting of two rubber threads are attached in a stretched state to peripheral edges of the respective leg-holes 12. Between these elastic members 13, 14 in the vertical direction as viewed in FIG. 1, the front and rear waist regions 6, 7 are provided with a plurality of auxiliary elastic members 16 attached in a stretched state thereto so as to extend in parallel one to another in a circumferential direction in order to provide a good fit of these front and rear waist regions 6, 7 to the wearer's body. Such diaper 1 includes an inner sheet 18 and an outer sheet 19 both configured in the pull-on type and placed one upon another. A body fluid absorbent pad 21 is attached to the inner surface of the inner sheet 18.

Figure 2:
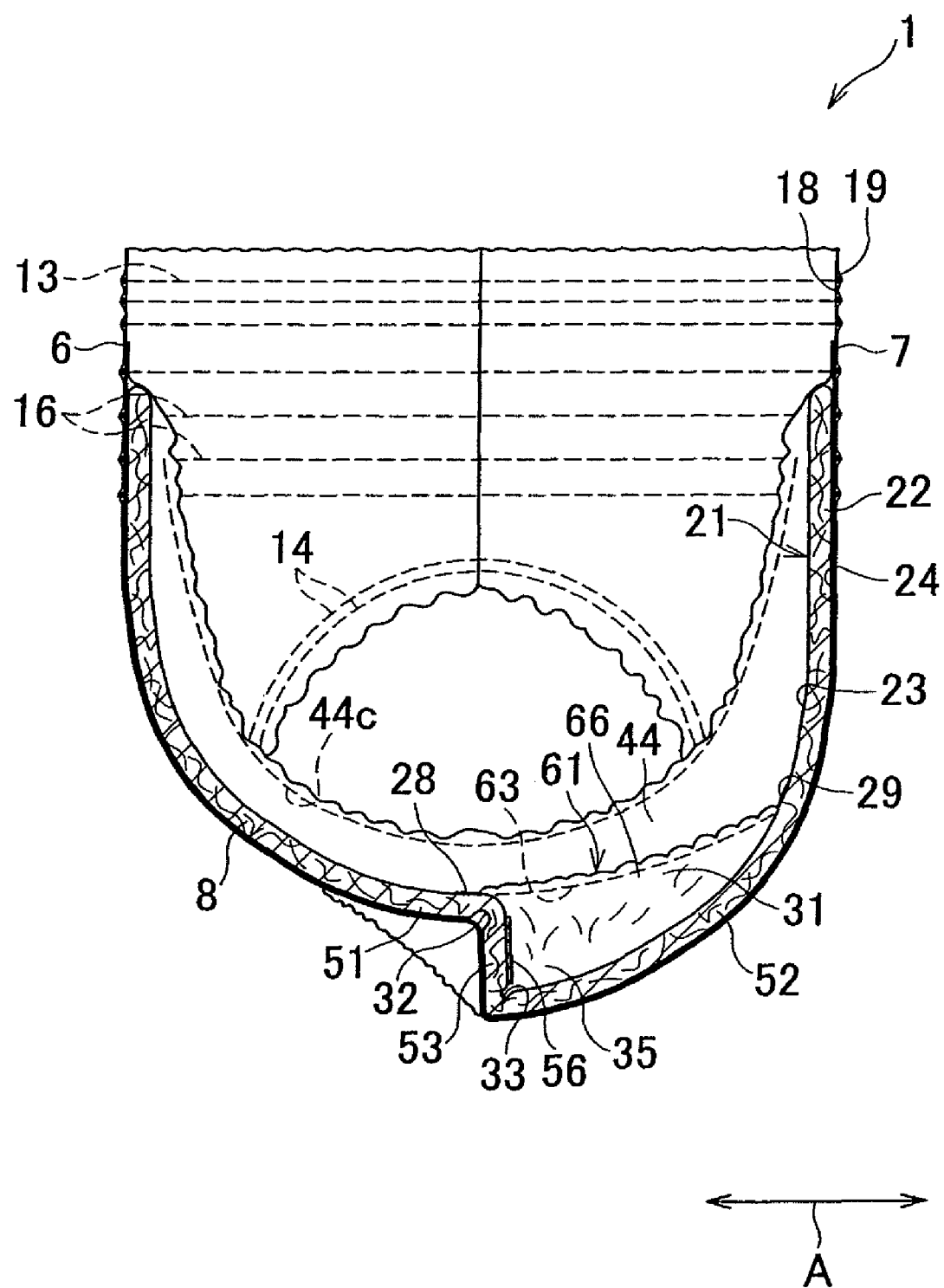
FIG. 2 is a sectional view taken along the line II-II in FIG. 1.

FIG. 2 is a sectional view taken along the line II-II in FIG. 1. The body fluid absorbent pad 21 extends in the crotch region 8 and further into the front waist region 6 as well as into the rear waist region 7. The body fluid absorbent pad 21 comprises a body fluid absorbent core 22, a liquid-pervious topsheet 23 and a liquid-impervious backsheet 24 sandwiching the core 22, a pair of leak-barrier cuffs 44 and a pair of contracting members 61. In the crotch region 8, the contracting members 61 are fixed to the topsheet 23 defining the inner surface of the pad 21 by adhesives 64 (See FIG. 3) or by appropriate sealing technique at respective front portions 28 thereof lying toward the front waist region 6 and at respective rear portions 29 thereof lying toward the rear waist region 7. Respective intermediate portions 31 extending the respective front portions 28 and the respective rear portions 29 are contracted in a horizontal direction as viewed in FIG. 2, i.e., in the longitudinal direction A of the diaper 1 under the effect of elastic members 63 consisting of rubber threads attached to these respective intermediate portions 31 and thereby spaced from the topsheet 23. While the pad 21 is normally in a state curved in the longitudinal direction A, the pad 21 is locally folded along a front folding guide groove 32 and a rear folding guide groove 33 upon contraction of the respective contracting members 61, as shown. Consequently, a depression 35 having an inner wall defined by the inner surface of the pad 21 is formed below the contracting members 61 so as to function as feces receiving space of the diaper 1. Both the waist-encircling elastic member 13 and the auxiliary elastic members 16 are interposed between the inner sheet 18 and the outer sheet 19 and bonded in a stretched state to at least one of these two sheets 18, 19.

Figure 3:
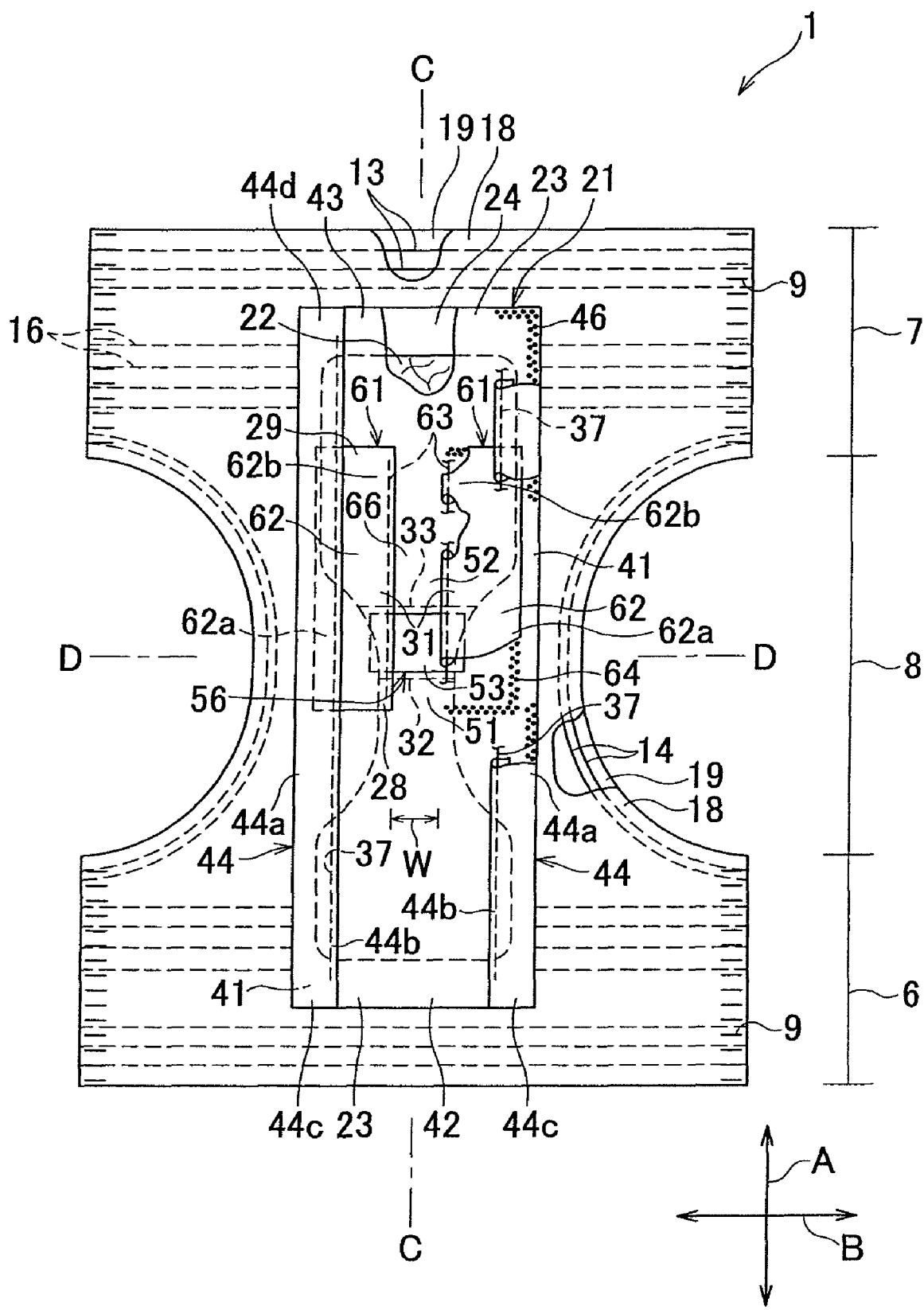
FIG. 3 is a partially cutaway plan view showing the disposable diaper of FIG. 1 developed in a longitudinal direction and in a transverse direction.

FIG. 3 is a partially cutaway plan view showing the diaper 1 with the front and rear waist regions 6, 7 as well as the crotch region 8 developed in the longitudinal direction A and in a transverse direction B orthogonal to the longitudinal direction A after the front and rear waist regions 6, 7 of the diaper 1 shown in FIG. 1 have been detached from each other at the sealing spots 9. Generally, the pad 21 comprises the hour-glass-shaped core 22 sandwiched between the topsheet 23 and the backsheet 24 both having a rectangular shape. These top- and backsheets 23, 24 extend outward beyond a peripheral edge of the core 22 and put flat and bonded together outside the peripheral edge of the core 22 by adhesives or appropriate sealing technique. The pad 21 is contoured by a pair of side edges 41 extending in the longitudinal direction A and front and rear ends 42, 43 respectively extending between the side edges 41. The respective side edges 41 are provided with leak-barrier cuffs 44 extending between the front and rear ends 42, 43. The leak-barrier cuffs 44 are formed from water-repellent, more preferably, a liquid-impervious non-woven fabric or plastic film. The leak-barrier cuffs 44 are bonded to the topsheet 23 by hot melt adhesives 46 along the respective outer side edges 44a as well as at front and rear ends 44c, 44d. The leak-barrier cuffs 44 respectively have, in addition, sleeve-shaped inner side edges 44b within which elastic members 37 consisting of rubber threads are attached in a stretched state. In the crotch region 8, the core 22 is formed at a position anterior to a transverse center line D-D bisecting a dimension of the diaper 1 as measured in the longitudinal direction A with the front folding guide 32 extending in the transverse direction B and at a position posterior to the transverse center line D-D with the rear folding guide 33 extending in the transverse direction B. These folding guides 32, 33 facilitate the pad 21 to be folded along them 32, 33 in response to curving of the crotch region 8 as a whole in the longitudinal direction A so that the pad 21 may be partially deformed as shown in FIG. 2. Specifically, the folding guides 32, 33 facilitate the pad 21 to form the depression 35 having the inner wall defined by the inner surface of the pad 21 and functioning as the feces receiving space. In the case of the diaper 1 for baby, the folding guides 32, 33 are spaced from each other preferably in a range of about 20 to about 50 mm. The pad 21 adapted to be folded comprises a front section 51 lying at a position anterior to the front folding guide 32, a rear section 52 lying at a position posterior to the rear folding guide 33 and an intermediate section 53 extending between these two sections 51, 52 (See FIG. 2). In this intermediate section 53, a block-shaped elastic member 56 (See FIG. 2) is attached by adhesives (not shown) to the topsheet 23 extending on the inner side of the intermediate section 53. The pad 21 is further provided with a pair of contracting members 61 intersecting with the intermediate section 53 and extending into the front section 51 as well as into the rear section 52 in a symmetrical relationship about a longitudinal center line C-C bisecting a width of the crotch region 8.

The block-shaped elastic member 56 on the intermediate section 53 serves to give this intermediate section 53 an appropriate stiffness and an appropriate restoring force characteristic. Such stiffness facilitates the pad 21 to be folded so that the intermediate section 53 may be oriented in the vertical direction of the diaper 1 as shown in FIG. 2 and the restoring force characteristic permits the position of the intermediate section 53 as shown in FIG. 2 to be quickly restored immediately after the intermediate section 53 has be released from the wearer's body weight bearing down thereupon. The preferred block-shaped elastic member 56 permits the elastic restoration of the intermediate section 53 having been deformed in the longitudinal direction (i.e., the longitudinal direction A in FIG. 3) and the transverse direction B of the diaper 1, at least in the longitudinal direction A. The more preferred block-shaped elastic member 56 permits the elastic restoration of the intermediate section 53 having been deformed in the longitudinal direction A as well as in the transverse direction.

The contracting members 61 bias the front section 51 and the rear section 52 to come close to each other in the longitudinal direction A as viewed in FIG. 3 so that the pad 21 may be folded along the front folding guide 32 and the rear folding guide 33 to form the feces receiving space in the crotch region 8. The contracting members 61 shown by FIG. 3 comprise a pair of strip-shaped sheets 62 respectively attached to the opposite sides and thread-shaped elastic members 63 attached, in a state thereof stretched in the longitudinal direction A, to the respective strip-shaped sheets 62. The contracting members 61 are bonded to the topsheet 23 by adhesives 64 not only at the front portions 28 and the rear portions 29 but also respective outer side edge portions 62a extending in parallel to the center line C-C. The elastic members 63 in the respective contracting members 61 are attached to the respective strip-shaped sheets 62 along inner side edges 62d extending in parallel to the center line C-C. The intermediate portions 31 including the elastic members 63 are not bonded to the topsheet 23 at the intermediate section 53 of the pad 21 and spaced from the topsheet 23 so as to be collapsible in the longitudinal direction A. The paired sheets 62 are spaced by a dimension W from each other in the transverse direction B so as to define an opening 66 (See FIG. 2 also) of the feces receiving space 35.

When this diaper 1 is put on the wearer's body, the waist-hole 11 is broadened and the crotch region 8 as a whole is curved substantially in a U-shape as shown in FIG. 1. Thereupon, the leak-barrier cuffs 44 in the crotch region 8 which are illustrated to be flat in FIG. 3 rise above the topsheet 23 under contracting effect of the elastic members 37. In other words, these leak-barrier cuffs 44 protrude toward inguinal region of the diaper wearer (not shown). Simultaneously, the elastic members 63 constituting the contracting member 61 in the pad 21 contract to bring the front section 51 and the rear section 52 close to each other and consequently the pad 21 is folded along the front folding guide 32 and the rear folding guide 33 so that the intermediate section 53 may be oriented in the vertical direction as seen in FIG. 2 to form the feces receiving space 35. The depth of the feces receiving space 35 depends on a dimension of the intermediate section 53 in the longitudinal direction A and an angle at which the intermediate section 53 rises with respective to its horizontal state. The feces receiving space 35 is provided along both sides of the opening opposite to each other in the transverse direction B with the strip-shaped sheets 62, respectively, so that the topsheet 23 in the front waist region 6, the strip-shaped sheets 62 and the topsheet 23 in the rear waist region 7 define together a substantially continuous smooth surface adapted to come in contact with the diaper wearer's skin. With the feces receiving space 35 formed in this manner, the surface destined to come in contact with the wearer's skin remains smooth and there is no anxiety that the wearer might experience any discomfortable feeling to wear the diaper 1 even if the depth of the feces receiving space is increased. In the feces receiving space 35, the intermediate section 53 stands upright so that relatively flowable feces once received in the feces receiving space 35 can be effectively prevented from backflowing to the front waist region 6. In this way, there is unlikely that the wearer's external genital organs might be soiled with feces. In addition, such feces receiving space 35 is covered with the strip-shaped sheets 62 except the opening 66 and thereby these strip-shaped sheets 62 is effective to alleviate a possibility that the wearer's skin might be soiled with feces collected in the feces receiving space 35. Such feces receiving space 35 is designed so that the opening 66 is opposed to the wearer's anus and the intermediate section 53 is interposed between the anus and the external genital organs. Even deformed once under the wearer's body weight bearing down thereupon, the intermediate section 53 having an elastic restoring force assured by the presence of the block-shaped elastic members 56 can its initial shape immediately after released from the wearer's body weight. In this way, the feces receiving space 35 can maintain its volume substantially constant.

In the diaper 1, as stock materials for the inner sheet 18 and the outer sheet 19, nonwoven fabrics or plastic films may be used wherein at least one of these two sheets may be of liquid-impervious nature. For the topsheet 23 constituting the pad 21, nonwoven fabrics or perforated plastic films may be used. For the backsheet 24, nonwoven fabrics or plastic films may be used. While the stock materials for the backsheet 24 is preferably liquid-impervious, it is possible to use liquid-pervious sheet materials as the backsheet 24 so far as the inner sheet 18 or the outer sheet 19 is liquid-impervious. For the core 22, water-absorbent materials such as fluff pulp or a mixture of fluff pulp and super-absorbent polymer particles may be used. The preferred core 22 comprises the water-absorbent material wrapped with a liquid-pervious sheet such as tissue paper. For the leak-barrier cuffs 44, nonwoven fabrics or plastic films which are preferably water-repellent or liquid-impervious. For the strip-shaped sheets 62 constituting the respective contracting members 61, elastically stretchable or inelastically stretchable or non-stretchable nonwoven fabrics or plastic films may be used. However, the contracting members 61 used in the illustrated embodiment respectively comprise thread-shaped elastic members 63 and therefore it is possible to use inelastically stretchable sheets or non-stretchable sheets for the sheets 62. Such sheets are advantageously inexpensive compared to the elastically stretchable sheets. When elastically stretchable sheet material is used for the strip-shaped sheets 62, it is preferred to bond the front portions 28, the rear portions 29 and the outer side edge portions, at least the front portions 28 and the rear portions 29 of these strip-shaped sheets 62 to the topsheet 23 without use of the elastic members 63. When such elastically stretchable strip-shaped sheets 62 are used, the number of steps required to make the diaper 1 may be reduced compared to the case in which non-stretchable strip-shaped sheets are used. As the block-shaped elastic member 56, a flexibly elastic foamed plastic sheet made of foamed polyurethane or foamed polyethylene, foamed polystyrene or the like or a sheet made of natural rubber or synthetic rubber or aggregate of synthetic fibers such as crimped fibers or rubber-based fibers, for example, nonwoven fabric sheets may be used. For the block-shaped elastic member 56, it is also possible to use tow comprising a plurality of straight synthetic fibers drawn in one direction and bundled in such a state. Assumed that the bundle of these synthetic fibers drawn in the longitudinal direction A in FIG. 3, the intermediate section 53 having been folded along the folding guides extending in the direction orthogonal to the direction in which the bundle of synthetic fibers extend can elastically restore the initial position.

Figure 4:
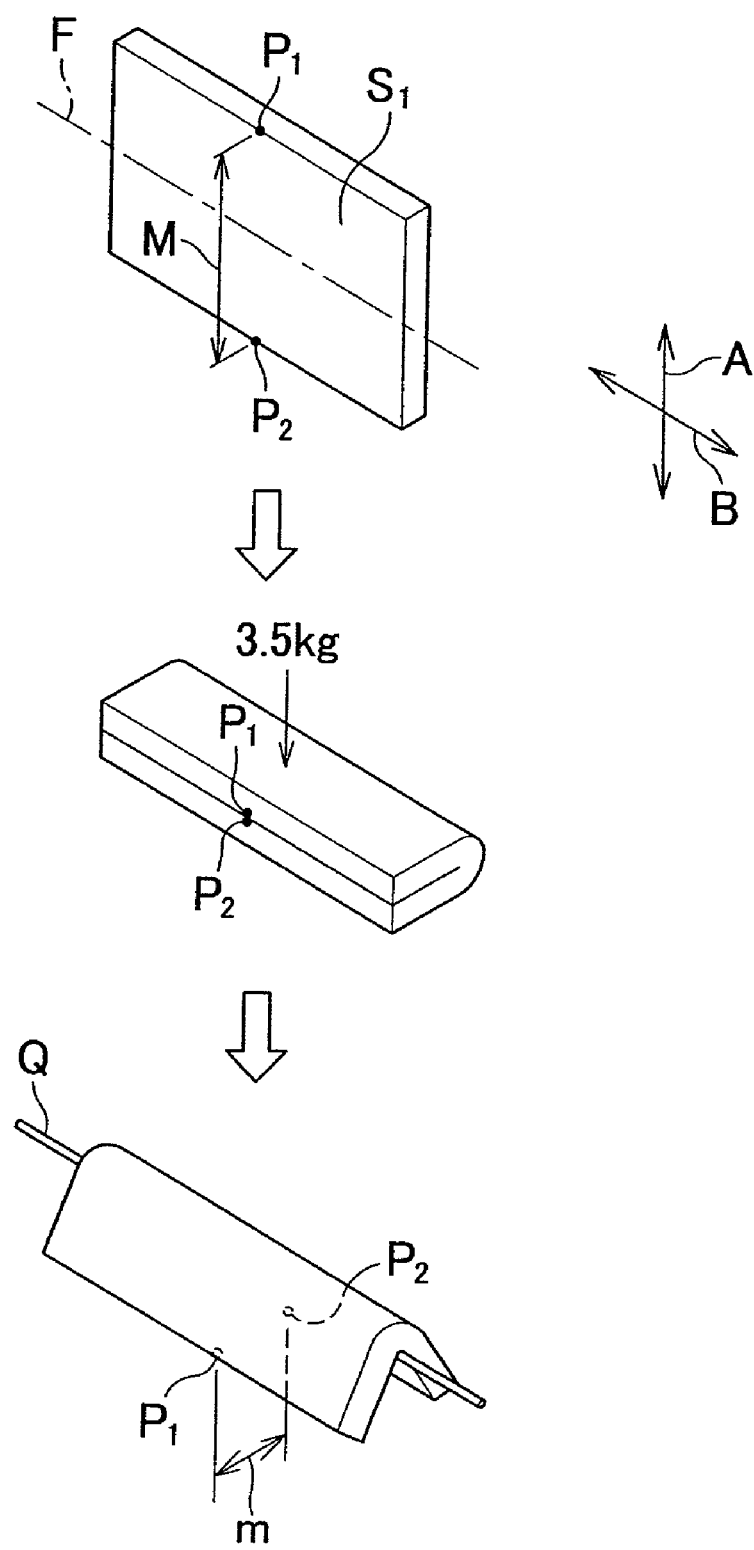
FIG. 4 is a diagram illustrating a method for evaluating an elastic restoring force of an intermediate zone.

FIG. 4 is a diagram schematically illustrating a method used to evaluate the elastic restoring force $F_A$ of the intermediate section 53 in the longitudinal direction A under the effect of the block-shaped elastic member 56. For this method for evaluation, a test specimen $S_1$ having a dimension of 30 mm in the longitudinal direction A and a dimension of 50 mm in the transverse direction B as viewed in FIG. 3 is cut off from the intermediate section including the block-shaped elastic member 56 so that the block-shaped elastic member 56 may centrally lie on this test specimen $S_1$. The test specimen $S_1$ cut off in this manner includes at least the topsheet 23, the backsheet 24, the inner sheet 18, the outer sheet 19 and the block-shaped elastic member 56 and may or may not include the core 22. This test specimen $S_1$ is left at rest for 1 minute in a petri dish having a diameter of about 10 cm and containing therein 10 ml of physiologic saline at a concentration of about 0.9% and then left at rest further for 1 minute on a glass plate. Subsequently, a direct distance M between two points $P_1$, $P_2$ lying on respective middles on lateral edges of the test specimen $S_1$ is exactly measured. Then the test specimen $S_1$ is folded back in the longitudinal direction A along a center line F connecting two points $P_1$, $P_2$ with the block-shaped elastic member 56 inside. The test specimen $S_1$ as a whole is then applied with a load of about 3.5 kg and left at rest under such load for 10 minutes. Then the test specimen $S_1$ released from such load is hung up on copper wire having a diameter of about 0.5 mm as illustrated and left at rest for 1 minute. Now a direct distance m between those two points $P_1$, $P_2$ of the test specimen $S_1$ having spread out by itself is exactly measured. The distance m/distance M (%) is determined as a value representing the elastic restoring force $F_A$ of the intermediate section 53 in the longitudinal direction A. The preferred embodiment of the invention adopts the block-shaped elastic member 56 exhibiting the elastic restoring force $F_A$ of 50% or higher.

The pad 21 may be formed with two grooves each having a width in a range of about 1 to about 5 mm and extending across the core 22 in the crotch region 8 as will be seen in FIG. 2 to obtain the front folding guide 32 and the rear folding guide 33. While these grooves can be obtained merely by locally compressing the core 22 in a V-shape or the like, the core 22 may be impregnated with water of about 10% by weight of the core 22 to obtain the grooves each of a higher density and of more clear contours. In the case of the core 22 containing thermoplastic synthetic fibers, the core 22 may be locally compressed under heating so as to melt the synthetic fibers and thereby to obtain the folding guides 32, 33 along which the core 22 is partially hardened. In the core 22 having a substantially uniform basis weight in the crotch region 8, it is possible to form the front folding guide 32 and the rear folding guide 33 by decreasing the basis weight of the portions corresponding to the grooves extending across the crotch region 8. Furthermore, the intermediate section in its entirety may be compressed so that the intermediate section 53 may have stiffness higher than those in the front section 51 and the rear section 52. In this way, a boundary line between the intermediate section 53 and the front section 51 defines the front folding guide 32 and a boundary line between the intermediate section 53 and the rear section 52 defines the rear folding guide 33. Furthermore, the front folding guide 32 and the rear folding guide 33 may be formed in a manner as will be described in reference with FIGS. 5, 6 and 7.

Figure 5:
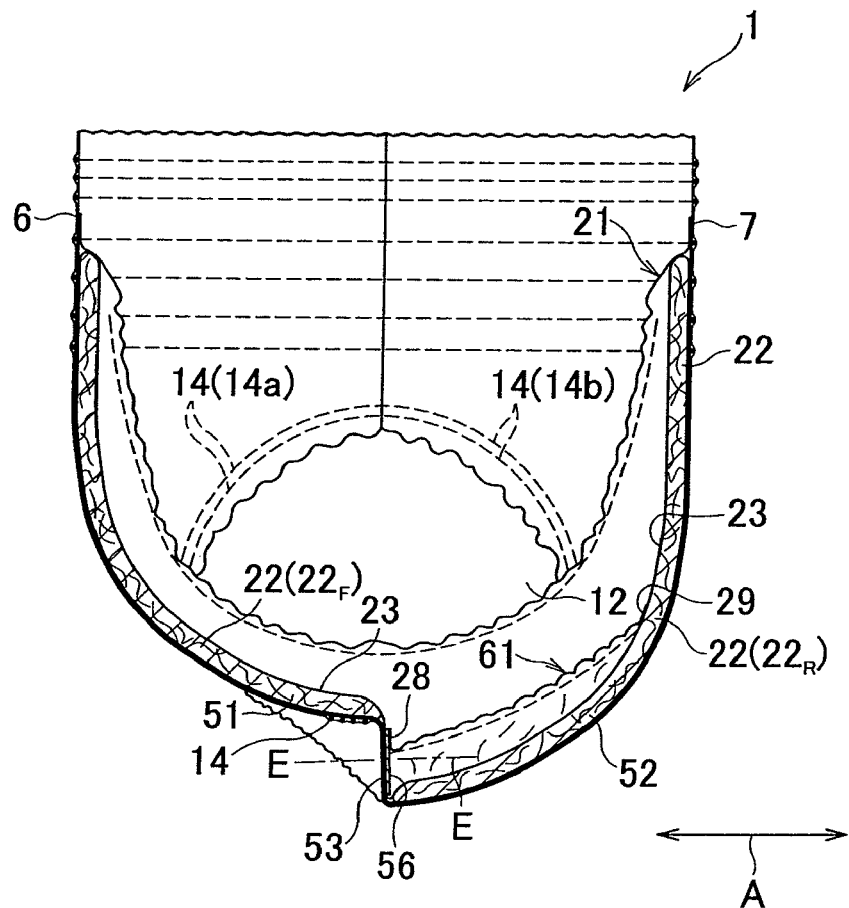
FIG. 5 is a view similar to FIG. 2, showing one preferred embodiment.
Figure 6:
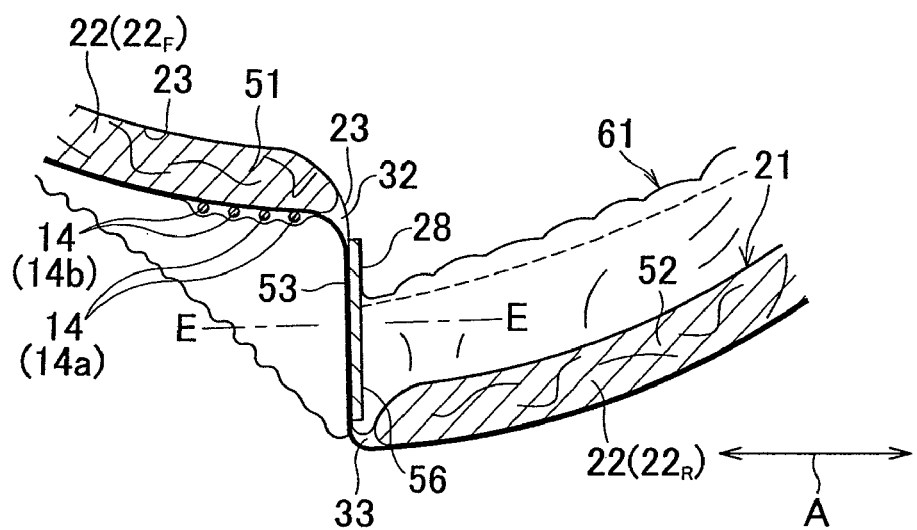
FIG. 6 is a view showing a part of FIG. 2 in an enlarged scale.
Figure 7:
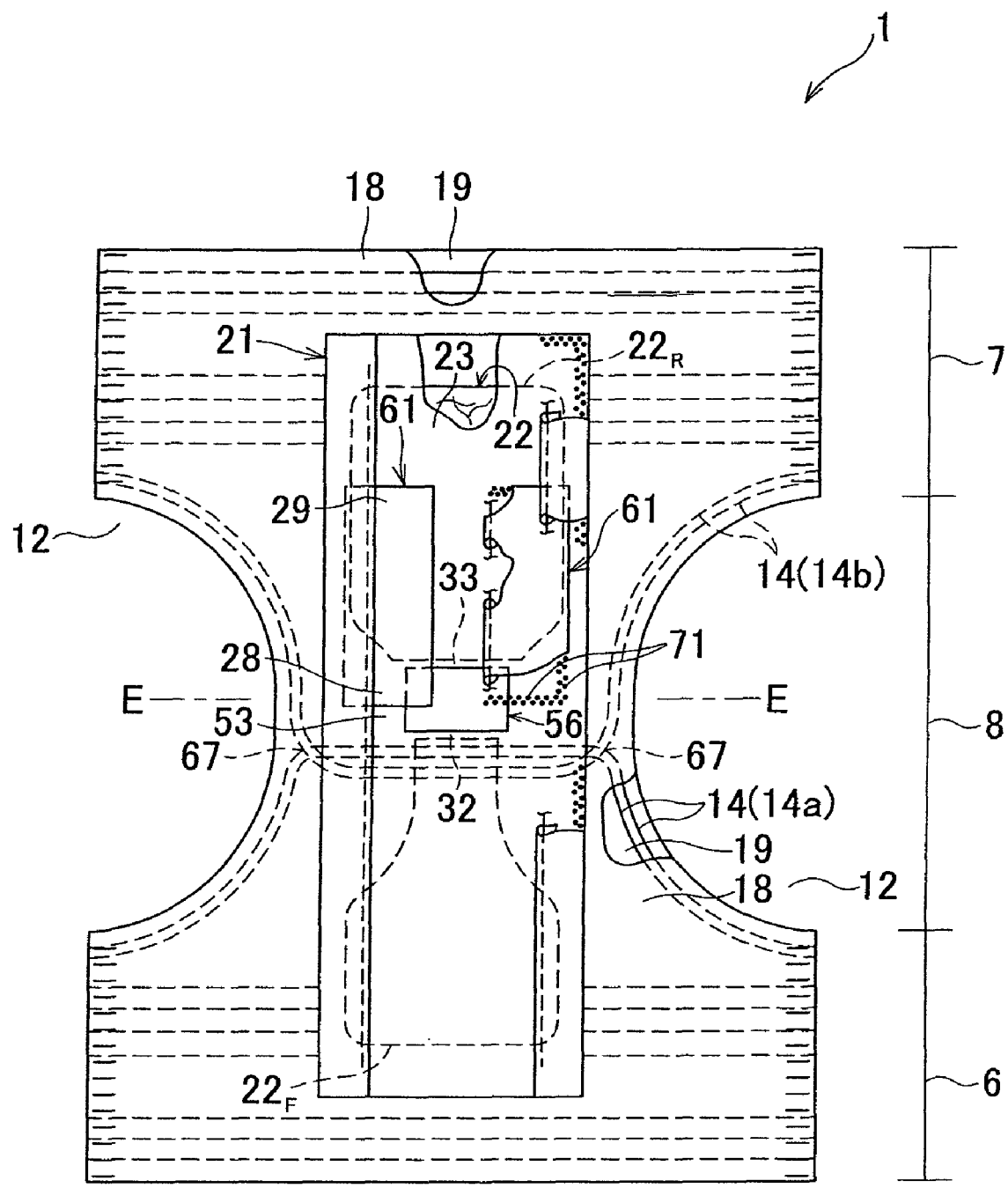
FIG. 7 is a view similar to FIG. 3, showing the diaper of FIG. 5.
Figure 7:
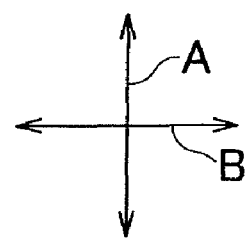

FIG. 5 is a view similar to FIG. 2, showing one preferred embodiment of the invention, FIG. 6 is a view showing a part of FIG. 2 in an enlarged scale and FIG. 7 is a view similar to FIG. 3. Referring to FIGS. 5, 6 and 7, the pad 21 is sized as the disposable diaper 1 for baby and has a length of about 400 mm and a width of about 140 mm. This diaper 1 includes the core 22 having a basis weight in a range of about 300 to about 700 g/m$^2$ and comprising a mixture of super-absorbent polymer particles of about 10 to about 40% by weight and fluff pulp of about 90 to about 60% by weight. It will be apparent from FIG. 7 that, in the crotch region 8, the core 22 is divided in the longitudinal direction into a front core $22_F$ and a rear core $22_R$ spaced from each other preferably by about 20 to about 50 mm. Between the front core $22_F$ and the rear core $22_R$, the block-shaped elastic member 56 is attached to the topsheet 23 by hot melt adhesives (not shown). The block-shaped elastic member 56 is formed, for example, by a flexible and elastic piece of foamed polyurethane having a thickness in a range of about 2 to about 7 mm and has a dimension in the longitudinal direction A slightly, for example, about 2 to about 10 mm smaller than a distance between the front core $22_F$ and the rear core $22_R$. A dimension of the block-shaped elastic member 56 in the transverse direction B may be either smaller or larger than a dimension of the core 22 as measured in the vicinity of the elastic member 56. This block-shaped elastic member 56 provided integrally with the topsheet 23 defines the intermediate section 53 in the diaper 1 shown by FIGS. 5 to 7 wherein groove-like zones each having a width of about 1 to about 5 mm and substantially devoid of the core 22 are defined between the front core $22_F$ and the block-shaped elastic member 56 and between the rear core $22_R$ and the block-shaped elastic member 56, respectively. These groove-like zones define the front folding guide 32 and the rear folding guide 33, respectively. Referring to FIG. 7, each of the leg-encircling elastic member 14 comprises a first leg-encircling elastic member 14a consisting of two rubber threads and a second leg-encircling elastic member 14b consisting also of two rubber threads. The first leg-encircling elastic member 14a extends, in stretched state, half around the peripheral edge of the leg-hole 12 (See FIG. 1) in a section of the crotch region 8 placed aside forward and across the front core $22_F$ in the crotch region 8. The second elastic member 14b extends, in a stretched state, half around the peripheral edge of the leg-hole 12 in a section of the crotch region 8 placed aside rearward and across the front core $22_F$ in the crotch region 8. The first elastic member 14a and the second elastic member 14b are intermittently bonded to the inner sheet 18 or the outer sheet 19 by adhesives (not shown). These first elastic member 14a and second elastic member 14b extend in parallel to the front folding guide 32 but intersect with each other in the vicinity of the associated one of the transversely opposite side edges of the crotch region to form a crossover site 67 which is, in turn, bonded to the inner sheet 18 or the outer sheet 19 by adhesives (not shown). Between a pair of such crossover sites 67, 67, these first and second elastic members 14a, 14b are in a state stretched in the transverse direction B so far as the diaper 1 is in its flattened state. When the diaper 1 is left free to take a curved shape as seen in FIG. 5, the first and second elastic members 14a, 14b contract in the transverse direction B, functioning to lift the front folding guide 32 with respect to the rear folding guide 33 (See FIGS. 5 and 6) and thereby to orient the intermediate section 53 in the vertical direction. Such function of these first and second elastic members 14a, 14b occurs in synchronism with the function of the contracting members 61 to orient the intermediate section 53 in the vertical direction. In the diaper 1 shown by FIGS. 5, 6 and 7, the dimension of the respective contracting members 61 as measured in the longitudinal direction A is shorter than the corresponding dimension of the respective contracting members 61 in the embodiment shown by FIG. 3 and the front portions 28 of the respective contracting members 61 are bonded, anteriorly to a center line E-E bisecting the dimension of the intermediate section 53 as measured in the longitudinal direction A, to the block-shaped elastic member 56 and also to the topsheet 23 lying outside the block-shaped elastic member 61 as viewed in the transverse direction B by adhesives 71. These contracting members 61 may contract between the front portions 28 and the rear portions 29, respectively, to pull the front zone of the intermediate section 53 rearward and thereby to orient the intermediate section 53 in the vertical direction as seen in FIGS. 5 and 6.

Figure 8:
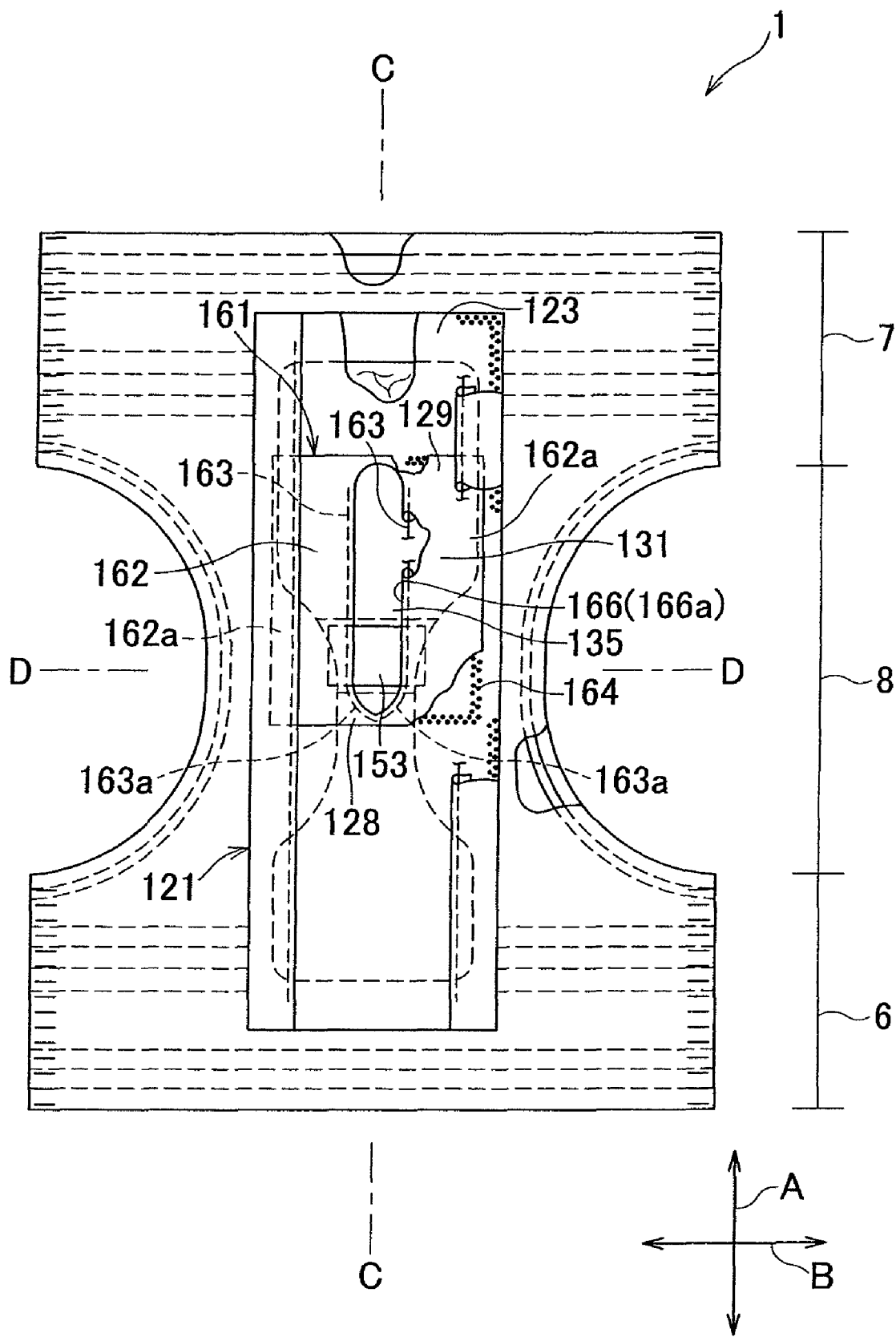
FIG. 8 is a view similar to FIG. 3, showing another preferred embodiment.

FIG. 8 also is a view similar to FIG. 3, showing another preferred embodiment of the invention. A contracting member 161 used in the diaper 1 according to the embodiment shown by FIG. 8 comprises a single sheet 162 of a nonwoven fabric or plastic film replacing a pair of sheets 62 used by the embodiment shown by FIG. 3. The sheet 162 is formed in the middle in the transverse direction B with an oval through-hole 166a extending in the longitudinal direction A. Along opposite side edges of this through-hole 166a, a pair of elastic members 163 consisting of rubber threads are bonded in a stretched state to the sheet 162. Front ends 163a of the respective elastic members 163 intersects with each other on the center line C-C. The contracting member 161 comprising the sheet 162 and the elastic members 163e has a front portion 128, a rear portion 129 and an intermediate portion 131 wherein the front portion 128 and the rear portion 129 are bonded to a topsheet 123 by hot melt adhesives 164. The contracting member 161 is bonded to the topsheet 123 also along outer lateral edges 162a. Substantially along the complete periphery of the through-hole 166a, the contracting member 161 is not bonded to the topsheet 123, i.e., free from the topsheet 123 and the lateral edges of the through-hole 166a opposed to each other in symmetry about the center line C-C contract in the longitudinal direction A so as to cooperate with the intermediate section 153 to form a feces receiving space 135 as shown in FIG. 2. The through-hole 166a defines an opening 166 for this feces receiving space 135. The contracting member 161 formed from a single sheet 162 in this manner advantageously reduces the number of members which would be otherwise required to make the diaper 1 and simplifies operation of attaching the contracting member to the pad 21. In this way, a cost required for making the diaper 1 may be reduced. Additionally, compared to the contracting members 61 of FIG. 3, the contracting member 161 is capable of covering the diaper wearer's body over a larger extent and thereby to alleviate an anxiety that the diaper wearer's skin might be soiled with feces once received in the feces receiving space. The sheet 162 may be replaced by an elastically stretchable nonwoven fabric or plastic film. In this case, the contracting member 161 is fixed to the pad 21 while this member 161 is stretched in the longitudinal direction A and the transverse direction B, at least in the longitudinal direction A. While it is not essential to bond the outer lateral edges 162a of the contracting member 161 to the pad 21 along full length of the respective outer side edges 162a, the outer side edges 162a may be bonded to the pad 21 along the full length thereof, if desired, to prevent body fluids from flowing in the transverse direction B by these outer lateral edges 162a.

Figure 9:
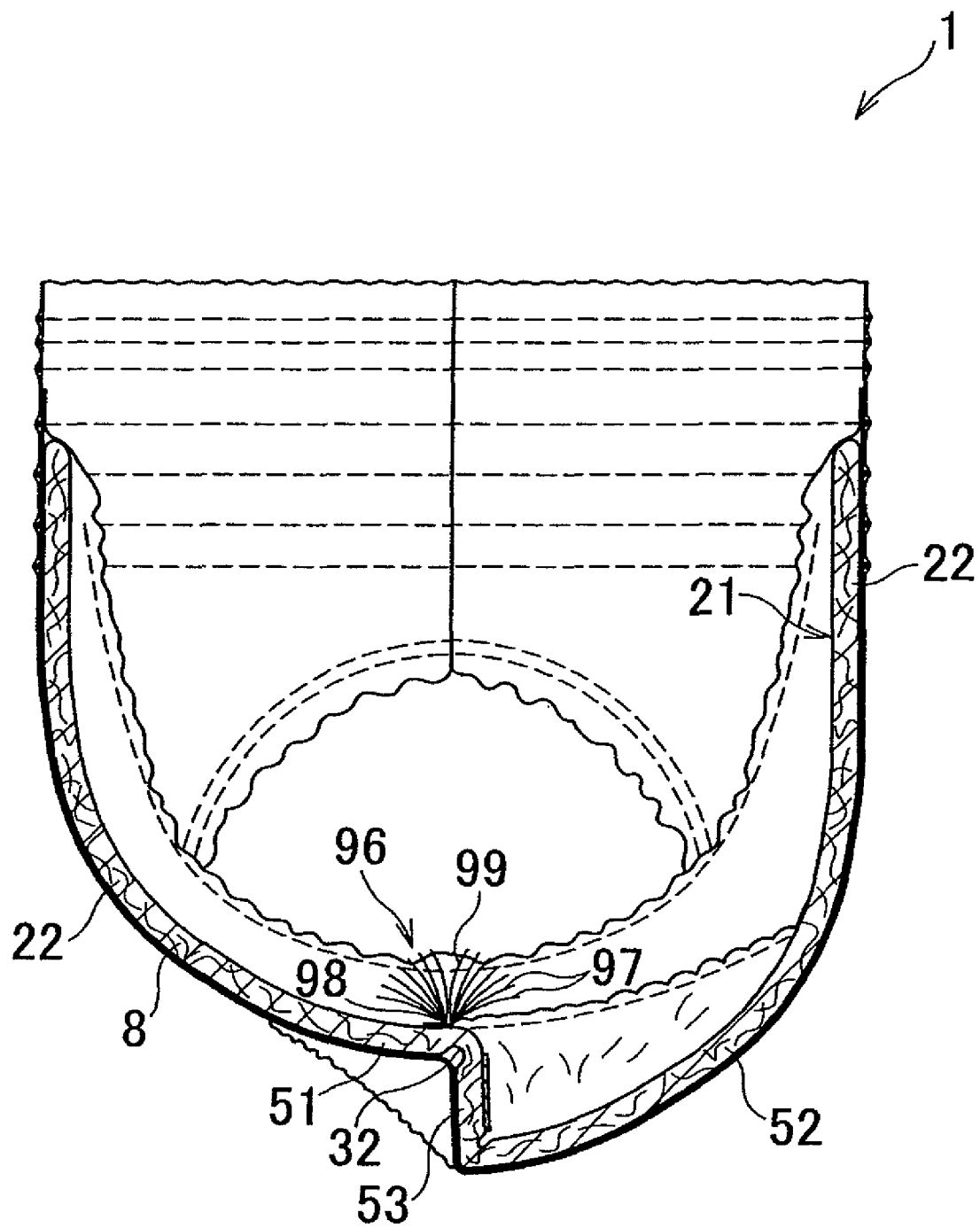
FIG. 9 is a view similar to FIG. 2, showing still another preferred embodiment.
Figure 10:
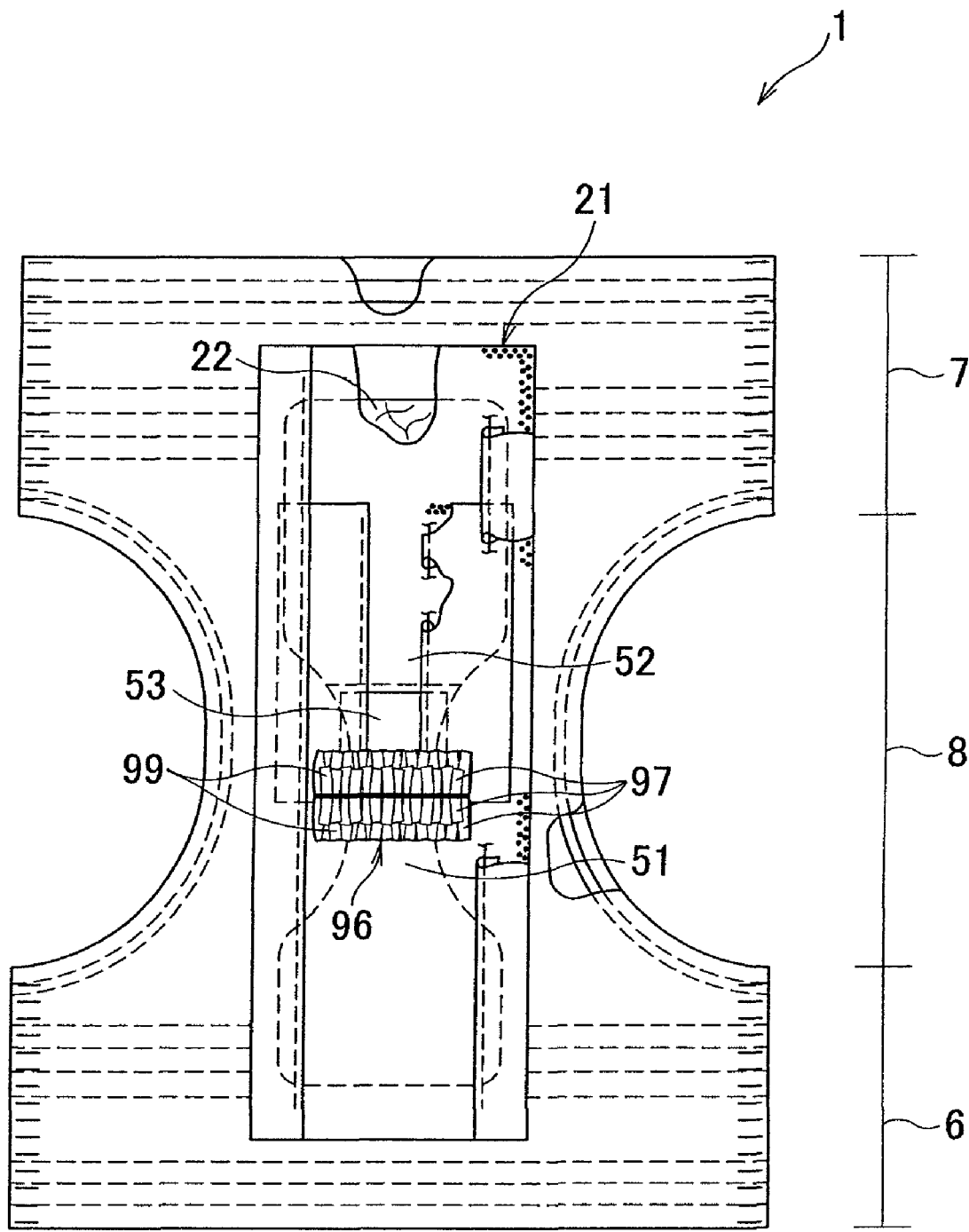
FIG. 10 is a view similar to FIG. 3, showing this preferred embodiment.

FIGS. 9 and 10 are views similar to FIGS. 2 and 3, respectively, showing still another preferred embodiment of the invention. In this diaper 1 of FIGS. 9 and 10, the front section of the pad 21 lying forward in the crotch region 8 is provided with a barrier 96. In the front section 51, the barrier 96 extends in the transverse direction B across the core 22 in the vicinity of the front folding guide 32 so as to stand in the way of urine tending to flow on the inner surface of the pad 21 from the front section 51 toward the intermediate section 53, on one hand, and to stand in the way of loose passage tending flow from the rear section and the intermediate section 53 toward the front section 51, on the other hand. Such barrier 96 comprises an assembly of strips 97 of nonwoven fabrics such as air-through nonwoven fabrics or spun bond nonwoven fabrics having a basis weight, for example, of 5 to 20 g/m$^2$ or plastic films such as polyethylene films having a thickness of 10 to 20 μm or paper such as tissue paper. These strips 97 have lower ends 98 bonded to the inner surface of the pad 21 and upper ends 99 left free so as to be movable and deformable (See FIG. 9). Size of the strips 97 depends on whether the diaper 1 is for baby or adult and, in the case of the diaper 1 for baby, a length of the strip 97 as measured from the inner surface of the pad 21 to the upper ends 99 is dimensioned preferably in a range of 5 to 30 mm and a width of the strip 97 is dimensioned preferably in a range of about 3 to about 10 mm. The barrier 96 functions also in a manner that the upper end 99 thereof gently rubs the diaper wearer's skin and thereby scrapes away loose passage or the like clinging to the wearer's skin.

Figure 11:
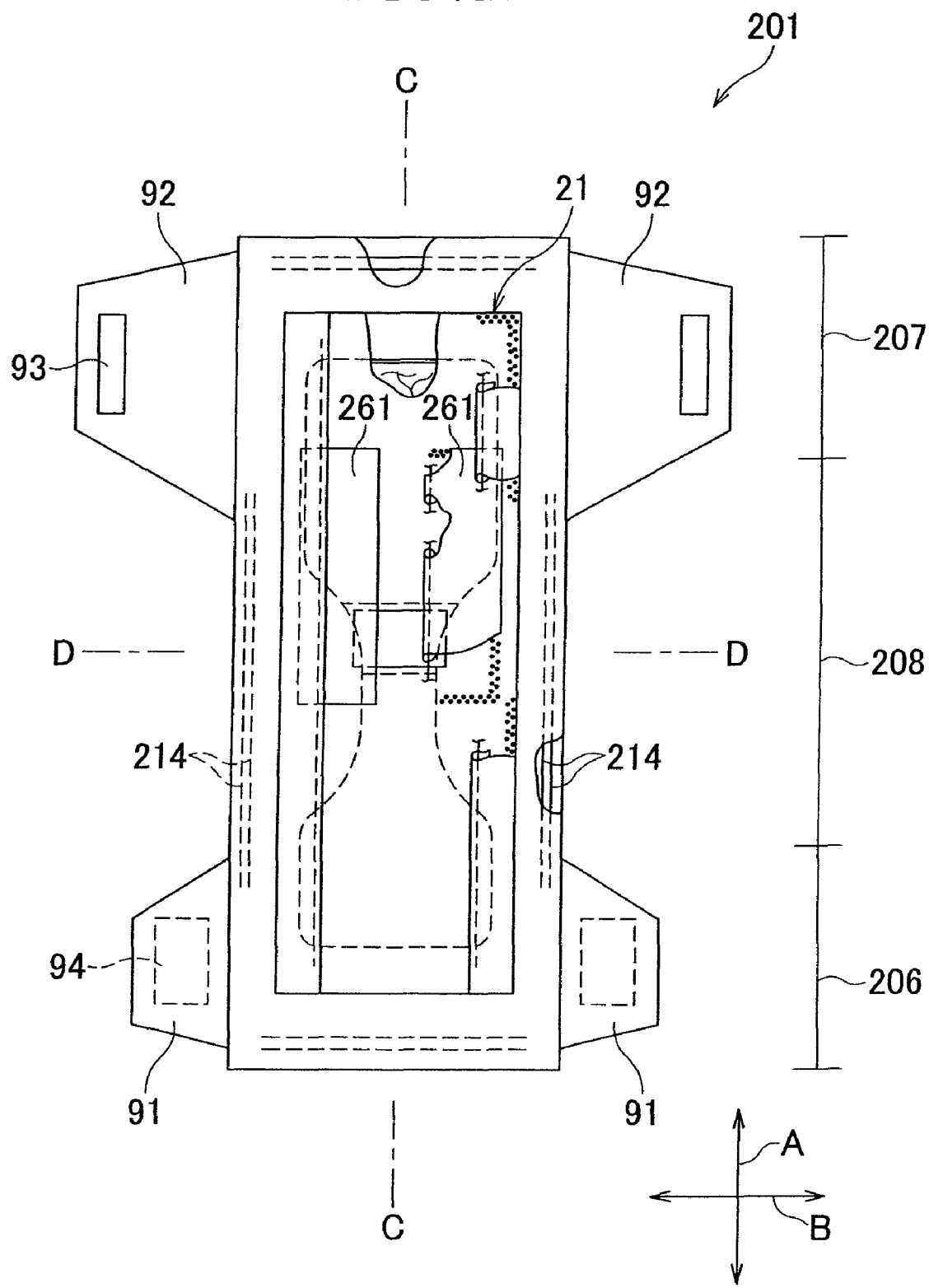
FIG. 11 is a view similar to FIG. 3, showing yet another preferred embodiment.

FIG. 11 also is a view similar to FIG. 3, showing yet another preferred embodiment of the invention. A diaper 201 according to the embodiment shown in FIG. 11 is distinguished from the diaper 1 of FIG. 3 in that the diaper 201 is of open-type, not of pull-on type. In the diaper 201 of FIG. 11, a front waist region 206 is provided along opposite side edges thereof with front wings 91, respectively, and a rear waist region 207 is provided along opposite side edges thereof with rear wings 92, respectively. The rear wings 92 are formed on inner surfaces thereof with pressure-sensitive adhesive applied zones 93 or hook member (of the so-called mechanical fastener) mounted zones replacing the pressure-sensitive adhesive applied zones 93. The front wings 91 are formed on outer surfaces thereof with target zones 94 to which those pressure-sensitive adhesive applied zones 93 or those hook member mounted zones replacing the pressure-sensitive adhesive applied zones 93 are adapted to be anchored. The diaper 201 includes leg-encircling elastic members 214 linearly extending in the longitudinal direction A and attached in a stretched state to opposite side edges of a crotch region 208. The further includes the same pad 21 as that used in the embodiment of FIG. 3.

The present invention can be exploited also as the open-type diaper 201. In the case of the pull-on type diaper 1 as shown in FIG. 1, the feces receiving space 35 having a sufficient depth as shown in FIG. 3 has already been formed when the diaper 1 is put on the wearer's body. Compared thereto, in the case of the usual open-type diaper 201, the feces receiving space must be formed under contracting effect of the contracting member 261 after the diaper has been put on the wearer's body. In any case, however, there is no anxiety that the wearer might experience a discomfortable feeling to wear because the feces receiving space is defined by a small portion of the crotch region even when the feces receiving space is relatively deep. Furthermore, the feces receiving space except the opening thereof is covered with the sheet-like contracting member (s) so that the inner surface of the diaper may be put in smooth contact with the wearer's skin over a wide range. From this viewpoint also, the disposable diaper according to the present invention will not create a feeling of discomfort against the wearer due to the presence of the feces receiving space which is relatively deep.

The present invention makes it possible to produce a disposable diaper which will not crate a feeling of discomfort against the wearer even if the depth of the feces receiving space is increased.

The entire discloses of Japanese Patent application No. 2006-105511 filed on Apr. 6, 2006 including specification, drawings and abstract are herein incorporated by reference in its entirety.

What is claimed is:
1. A disposable diaper, comprising:
a front waist region, a rear waist region, and a crotch region extending between the front and the rear waist regions in a longitudinal direction of the diaper,
wherein said crotch region has
a front folding guide and a rear folding guide extending in parallel to each other in a transverse direction orthogonal to the longitudinal direction,
a front portion, a rear portion and an intermediate portion, said front folding guide located between the front portion and the intermediate portion, said rear folding guide located between the intermediate portion and the rear portion,
an inner surface adapted to face a wearer's skin and an outer surface adapted to face away from said wearer's skin,
leg-encircling elastic members attached to lateral edges of the crotch region, respectively,
a feces receiving space defined between said leg-encircling elastic members and extending along said lateral edges,
a pair of leak-barrier cuffs extending in the longitudinal direction; and
a pair of contracting members between said leak-barrier cuffs, spaced from each other in said transverse direction, extending across said intermediate portion, and elastically contractible in said longitudinal direction; and
wherein
each of said contracting members includes front and rear sections and an intermediate section extending between the front and rear sections in the longitudinal direction, wherein
said front sections are fixed to said inner surface at positions anterior to a line bisecting a length of said intermediate section in said longitudinal direction,
said rear sections are fixed to said inner surface at positions posterior to said intermediate section, and
said intermediate sections are free of direct attachment to said inner surface so as to be elastically contractible in the longitudinal direction; and
upon contraction of said contracting members, said crotch region is folded downward in a vertical direction along said front folding guide and said rear folding guide to form, between said contracting members in the vicinity of said intermediate section, said feces receiving space,
the disposable diaper further includes a block-shaped elastic member bonded directly onto the inner surface at the intermediate portion of the crotch region for rendering said intermediate portion elastically deformable.

2. The disposable diaper as defined by claim 1, wherein said block-shaped elastic member is at least one selected from the group consisting of (i) a sheet made of material including at least one of foamed polyurethane, foamed polyethylene, foamed polystyrene, natural rubber or synthetic rubber, (ii) an assembly of crimped synthetic fibers and (iii) an assembly of plural synthetic fibers straightened in parallel one to another.

3. The disposable diaper as defined by claim 1, wherein
said contracting members further comprise a pair of strip-shaped sheets adapted to be elastically stretchable, and extending in said longitudinal direction in parallel to each other, and
in an elastically stretchable condition, each of said strip-shaped sheets includes an inner side edge and an outer side edge, wherein said inner side edge lies nearer to a central line of said crotch region than the respective outer side edge, and
said front section and said rear section are fixed to said inner surface so as to form an opening of the feces receiving space between said inner side edges of said strip-shaped sheets.

4. The disposable diaper as defined by claim 1, wherein
said contracting members further comprise a pair of strip-shaped sheets adapted to be non-stretchable or inelastically stretchable, and elastic threads, said elastic threads attached in a stretched state to said strip-shaped sheets, and extending in said longitudinal direction in parallel to each other in an elastically stretchable condition,
in a relaxed condition, each of said strip-shaped sheets includes an inner side edge and an outer side edge, wherein the inner side edge lies nearer to a central line of said crotch region than the respective outer side edge,
said elastic members are attached to said inner side edges, and
said front section and said rear section are fixed to said inner surface so as to form an opening of the feces receiving space between said inner side edges of said strip-shaped sheets.

5. The disposable diaper as defined by claim 3, wherein said strip-shaped sheets are fixed to said inner surface along said outer side edges, respectively.

6. The disposable diaper as defined by claim 1, wherein said contracting members comprises an elastically stretchable single sheet having said front section, said rear section, said intermediate section and
a through-hole provided in the middle of the sheet in said transverse direction so as to define an opening, said sheet being stretched in said longitudinal direction and fixed, in a stretched state, to said inner surface at said front section and said rear section while said intermediate section is left free from said inner surface along a peripheral edge of said through-hole.

7. The disposable diaper as defined by claim 1, wherein said contracting members comprises an elastically stretchable single sheet having said front section, said rear section, said intermediate section and
a through-hole provided in the middle of the sheet in said transverse direction so as to define an opening, said sheet being fixed to said inner surface at said front section and said rear section and, in the vicinity of opposite side edges of said through-hole extending in said longitudinal direction, elastic members being attached in stretched state to said single sheet so as to leave said intermediate section free from said inner surface along a peripheral edge of said through-hole.

8. The disposable diaper as defined by claim 1, wherein said contracting members extend into the front and rear portions of the crotch region but do not extend into the rear waist region.

9. The disposable diaper as defined by claim 1, wherein said leg-encircling elastic members comprise a front leg-encircling elastic member and a rear leg-encircling elastic member,
said front elastic member having opposite end sections extending along front halves of the lateral edges of the crotch region, and a middle section extending in the transverse direction across the crotch region, and
said rear elastic member having opposite end sections extending along rear halves of the lateral edges of the crotch region, and a middle section extending in the transverse direction across the crotch region.

10. The disposable diaper as defined by claim 9, wherein
said front and rear elastic members intersect with each other in a vicinity of the lateral edges in the transverse direction to define crossover sites which are directly bonded to the inner sheet, and
upon contraction, in the longitudinal direction of the middle sections of the front and rear elastic members between the crossover sites, the crotch region is folded downward in the vertical direction along the front folding guide and the rear folding guide.

11. The disposable diaper as defined by claim 3, wherein said strip-shaped sheets are directly fixed to the inner sheet at said front section and said rear section and also at the outer side edges.

12. The disposable diaper as defined by claim 1, wherein said front sections of the contracting members are directly bonded to the intermediate portion of the crotch region at the positions anterior to the line bisecting the length of said intermediate section in said longitudinal direction.

13. The disposable diaper as defined by claim 1, wherein said front sections of the contracting members are directly bonded to the block-shaped elastic member.

14. The disposable diaper as defined by claim 9, wherein said both middle sections of the elastic members are located rearward of the rear folding guide.

15. A disposable diaper, comprising:
a front waist region, a rear waist region, and a crotch region extending between the front and the rear waist regions in a longitudinal direction of the diaper,
wherein said crotch region has
a front folding guide and a rear folding guide extending in parallel to each other in a transverse direction orthogonal to the longitudinal direction,
a front portion, a rear portion and an intermediate portion, said front folding guide located between the front portion and the intermediate portion, said rear folding guide located between the intermediate portion and the rear portion,
an inner surface adapted to face a wearer's skin and an outer surface adapted to face away from said wearer's skin,
leg-encircling elastic members attached to lateral edges of the crotch region, respectively,
a feces receiving space defined between said leg-encircling elastic members and extending along said lateral edges,
a pair of leak-barrier cuffs extending in the longitudinal direction; and
a pair of contracting members between said leak-barrier cuffs, spaced from each other in said transverse direction, extending across said intermediate portion, and elastically contractible in said longitudinal direction; and wherein each of said contracting members includes front and rear sections and an intermediate section extending between the front and rear sections in the longitudinal direction, wherein said front sections are fixed to said inner surface at positions anterior to a line bisecting a length of said intermediate section in said longitudinal direction, said rear sections are fixed to said inner surface at positions posterior to said intermediate section, and said intermediate sections are free of direct attachment to said inner surface so as to be elastically contractible in the longitudinal direction; and upon contraction of said contracting members, said crotch region is folded downward in a vertical direction along said front folding guide and said rear folding guide to form, between said contracting members in the vicinity of said intermediate section, said feces receiving space, the disposable diaper further includes an absorbent core continuously extending in the crotch region and having an inner surface and an outer surface opposite to the inner surface, said inner surface of the absorbent core defining the inner surface of the diaper in the crotch region, wherein the front folding guide is provided on the outer surface of the absorbent core and the rear folding guides is provided on the inner surface of the absorbent core, and wherein the front folding guide and the rear folding guides are grooves which are compressed from the outer surface of the absorbent core and the inner surface of the absorbent core, respectively.

\* \* \* \* \*